(12) United States Patent
Genaro

(10) Patent No.: US 8,042,206 B2
(45) Date of Patent: Oct. 25, 2011

(54) BED EXIT ALARM

(75) Inventor: David M. Genaro, North Lauderdale, FL (US)

(73) Assignee: Anodyne Medical Device, Inc., Coral Springs, FL (US)

( * ) Notice: Subject to any disclaimer, the term of this patent is extended or adjusted under 35 U.S.C. 154(b) by 132 days.

(21) Appl. No.: 12/558,142

(22) Filed: Sep. 11, 2009

(65) Prior Publication Data

US 2011/0061164 A1   Mar. 17, 2011

(51) Int. Cl.
G08B 21/00 (2006.01)
A44C 21/00 (2006.01)

(52) U.S. Cl. .................. 5/424; 5/732; 5/713; 340/573.1

(58) Field of Classification Search ............. 5/424, 713, 5/732; 340/573.1
See application file for complete search history.

(56) References Cited

U.S. PATENT DOCUMENTS

| | | | |
|---|---|---|---|
| 3,533,095 A * | 10/1970 | Collins | 340/573.3 |
| 4,175,263 A * | 11/1979 | Triplett et al. | 340/573.4 |
| 4,179,692 A | 12/1979 | Vance | |
| 4,295,133 A | 10/1981 | Vance | |
| 4,484,043 A | 11/1984 | Musick et al. | |
| 4,565,910 A | 1/1986 | Musick et al. | |
| 4,700,180 A | 10/1987 | Vance | |
| 4,907,845 A * | 3/1990 | Wood | 340/573.4 |
| 5,184,112 A * | 2/1993 | Gusakov | 340/573.1 |
| 5,235,319 A | 8/1993 | Hill et al. | |
| 5,410,297 A | 4/1995 | Joseph et al. | |
| 6,583,727 B2 * | 6/2003 | Nunome | 340/665 |
| 6,778,090 B2 | 8/2004 | Newham | |
| 6,877,178 B2 * | 4/2005 | Chapman et al. | 5/713 |
| 7,656,299 B2 * | 2/2010 | Gentry et al. | 340/573.1 |
| 7,735,171 B2 * | 6/2010 | Kan | 5/732 |
| 2009/0183312 A1 * | 7/2009 | Price et al. | 5/706 |

* cited by examiner

Primary Examiner — Michael Trettel
(74) Attorney, Agent, or Firm — Nixon & Vanderhye P.C.

(57) ABSTRACT

A bed exit detecting system cooperable with a mattress includes a pair of bolster air cells respectively positionable adjacent opposite sides of the mattress. A pressure source is provided in fluid communication with the bolster air cells, and a pressure sensor is connected to the air cells. A signal processor communicating with the pressure sensor and the pressure source includes an alarm that is activated when a predetermined pressure change in one of the air cells is detected by the pressure sensor.

16 Claims, 2 Drawing Sheets

BED EXIT ALARM

CROSS-REFERENCES TO RELATED APPLICATIONS (NOT APPLICABLE)

STATEMENT REGARDING FEDERALLY SPONSORED RESEARCH OR DEVELOPMENT (NOT APPLICABLE)

BACKGROUND OF THE INVENTION

The invention relates to a bed exit alarm and, more particularly, to a bed exit alarm using pressure feedback from side bolsters on a support surface.

Care givers in a hospital or other treatment/care facility often must be able to know when a patient remains in a medical bed or chair, or has removed themselves. Unassisted bed exits can cause patient harm or injury, even losing patients in the facility if the patient becomes disoriented.

It is desirable to have some sort of notification/monitoring system of these unplanned bed/chair exits. There are many systems that claim to do this.

U.S. Pat. Nos. 4,484,043 and 4,565,910 describe devices that use a switch mechanism which is used to open and close a circuit to indicate the exit from a bed. The switches are basically two long conductors that make contact when the patient's body weight is on them. A closed switch indicates that the patient is in bed. The reverse happens when the patient exits; the conductors move apart, the switch opens and a bed exit is indicated.

U.S. Pat. No. 6,778,090 describes a capacitive array housed within a thin mat, which is placed either under the patient or under the mattress itself. This capacitance device detects a dielectric shift induced capacitive changes brought about by either the presence or absence of a patient on the bed.

U.S. Pat. No. 5,410,297 also describes a capacitive sensor pad device with a foam and aluminum foil pad. The pad under the patient has weight responsive capacitance characteristics that vary with the patient's weight and movement.

U.S. Pat. Nos. 4,179,692 and 4,295,133 disclose a system in which an on/off switch generates binary signals in response to the movements of the patient in and out of bed.

U.S. Pat. No. 4,700,180 also uses a binary generating sensor. When the patient lies down, the first switch position is established. When the patient exits the bed, the switch changes to its alternate state, thereby providing a binary signal.

U.S. Pat. No. 5,235,319 describes another capacitor sensor device at a predetermined location in the bed used in conjunction with a monitoring circuit system.

All of the above devices and other similar art have several disadvantages. The first and most problematic is that these sensing or capacitance devices are placed in pads which are either directly under the patient or under the mattress. If the pad is placed directly under the patient, it must be very thin and flexible so as not to increase the pressure on the bony protuberances of the patient. If the sensing pad is under the mattress, it loses its effectiveness as all inputs and outputs from the sensing pad must travel through the mattress. For instance, as the patient shifts their weight to exit the bed, due to the thick and "stiff" mattress, the weight distribution might be significantly distorted, causing the bed exit alarm not to work properly. Secondly, there is a lot of sophisticated circuitry and there are many components required to make these complicated capacitance or switch systems work, leading to higher costs, and greater chances of malfunctions.

BRIEF SUMMARY OF THE INVENTION

It is therefore desirable to have a very simple, reliable, and cost effective out-of-bed exit alarm system. It would also be desirable to have notification of patient entrapment along the side of the bed, between the side rails and bed frame.

Patient movement on a pneumatic support surface results in pressure changes in the various air cells, dependent on weight distribution. An air cell or a zone of air cells in a support surface will have a preset pressure maintained. As the patient moves onto this air cell, the pressure will temporarily rise due to a decreased size of air cell (e.g., as the patient makes it flat) yet the amount of air originally in the air cell remains constant for a least some time. If this air cell is connected to others, it will eventually bleed air out to the other adjoining cells, to equalize and balance the air cell pressure.

On some systems, the electronic controller will sense this change of pressure and compensate for it by either inflating and/or deflating the air cells to once again achieve the preset pressure. As the electronic controller already knows of the pressure change in the air cell, or in a zone, it is relatively easy to use this information to sound an alarm or other means of notification.

If narrow air cells are placed along the perimeter (sides) of the bed and filled to a set pressure, patient egress or potential entrapment can be detected by sensing the increase in cell pressure caused by the patient's body weight exerting additional pressure on these perimeter cells.

In an exemplary embodiment, a bed exit detecting system cooperable with a mattress includes a pair of bolster air cells respectively positionable adjacent opposite sides of the mattress. A pressure source is provided in fluid communication with the bolster air cells, and a pressure sensor is connected to the air cells. A signal processor communicating with the pressure sensor and the pressure source includes an alarm that is activated when a predetermined pressure change in one of the air cells is detected by the pressure sensor. This pressure could be a fixed value, or calculated internally based on patient weight and desired sensitivity. In one embodiment, the bolsters extend along a full length of the mattress.

The signal processor may be programmed to maintain a predetermined pressure in the air cells via the pressure source. The signal processor may be further programmed to activate the alarm when the predetermined pressure change is detected for a predetermined period of time, for example, about five seconds.

Preferably, the pressure sensor is a pressure transducer in fluid communication with the air cells.

In one arrangement, the bed exit detecting system includes a mattress overlay to which the pair of bolster air cells is attached. The mattress overlay is sized to fit on top of the mattress. The system may also include a component housing containing the signal processor, the pressure source, and the pressure sensor, where the pressure source is connected to the air cells via tubing.

The bolster air cells may be baffled bolsters having a cross section that is taller than it is wide.

In another exemplary embodiment, a bed exit detecting system cooperable with a mattress includes a housing, a pair of bolster air cells under pressure and respectively positionable adjacent opposite sides of the mattress, a pressure sensor mounted in the housing and communicating with the air cells, and a signal processor mounted in the housing and communicating with the pressure sensor. The signal processor includes an alarm that is activated when a predetermined pressure increase in one of the air cells is detected by the pressure sensor.

In yet another exemplary embodiment, a hospital bed includes a bed frame, a mattress secured to the bed frame, and the bed exit detecting system of the described embodiments.

BRIEF DESCRIPTION OF THE DRAWINGS

These and other aspects and advantages will be described in detail with reference to the accompanying drawings, in which.

DETAILED DESCRIPTION OF THE INVENTION

Figure 1:
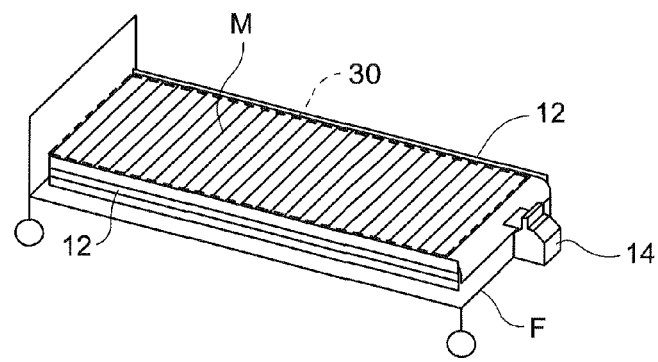
FIG. 1 is a perspective view of a bed and mattress including the bed exit detecting system of the described embodiments.

With reference to the drawings, the bed exit detecting system includes a pair of bolster air cells 12 respectively positionable adjacent opposite sides of a mattress M. Although a pneumatic mattress M is shown, the bed exit detecting system may be configurable for operation with a conventional mattress. The system components are preferably secured within a housing 14. The system includes a pressure source 16, such as a pump, in fluid communication with the bolster air cells 12. A pressure sensor 18, such as a pressure transducer, is connected directly with the bolster air cells 12 via tubing or the like. A signal processor 20, such as a microcontroller, communicates with the pressure sensor 18 and the pressure source 16 and includes an alarm 22 that is activated when a predetermined pressure change (increase) in one of the air cells 12 is detected by the pressure sensor 18. It is preferable that the bolster air cells 12 extend along a full length of the mattress end as shown, although a shorter length could be conceivable depending on side rail arrangements of the bed frame F.

The signal processor 20 is programmed to maintain a predetermined pressure, such as 50 mmHg in the air cells 12 via the pressure source 16. In an exemplary construction, the signal processor 20 controls a solenoid valve 24 to connect the pressure source 16 with the air cells 12. When the pressure sensor 18 detects a pressure change in the bolster air cells 12 by some predetermined level, a signal is sent to the alarm 22. The pressure change could be a fixed value, e.g., 7 mmHg, or calculated internally based on patient weight and desired sensitivity. In a preferred embodiment, the signal processor 20 is programmed to activate the alarm 22 when the predetermined pressure change is detected for a predetermined period of time. An exemplary period of time is about 5 seconds. With the pressure increase over the specified time, a clear indication of bed or chair egress or an entrapment issue can be detected.

Figure 2:
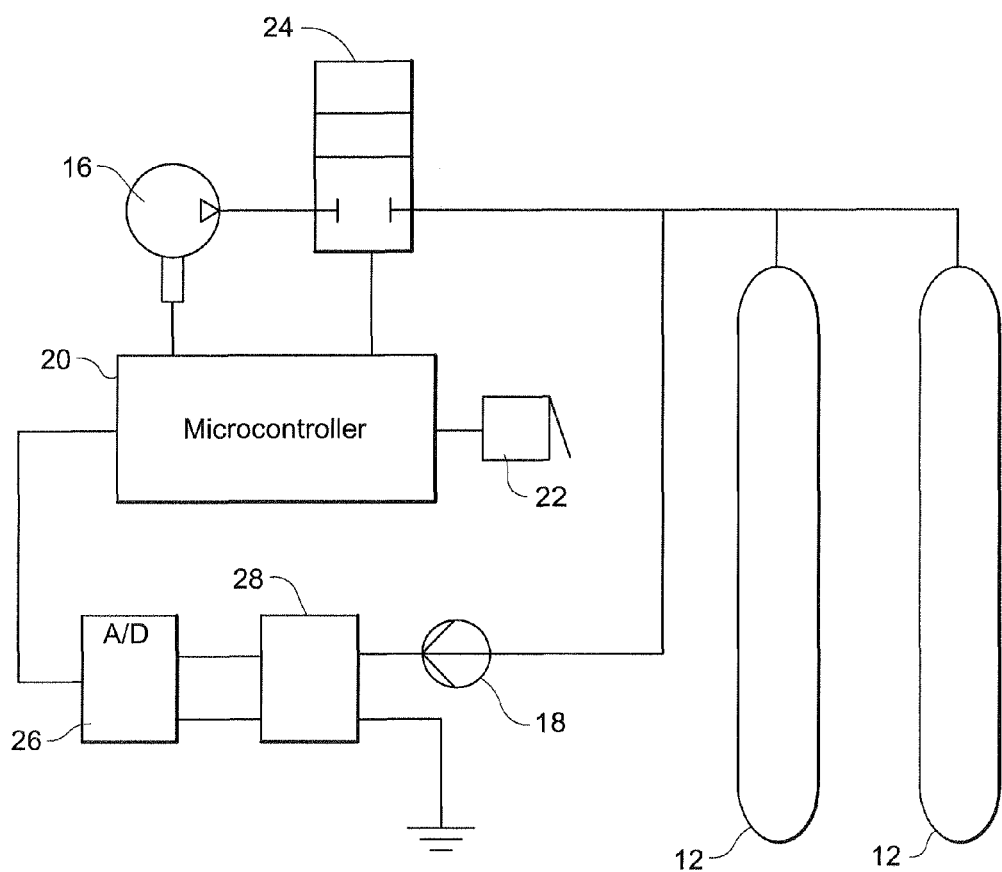
FIG. 2 is a schematic diagram of the bed exit detecting system.

With continued reference to FIG. 2, the pressure sensor 18 is connected directly to the air cells 12 via tubing or the like. This allows accurate and immediate (within microseconds) measurement of pressure changes. The sensor signal is digitized via an analog-to-digital (A/D) converter. The signal may be amplified via an amplifier 28, or used as is, and is read by the signal processor 20. The signal processor 20 monitors the pressure changes and, in the preferred embodiment, also monitors time. As noted, when certain parameters are met, the processor sends a signal to the alarm 22 for alarm notification.

This system is advantageous relative to other systems in that it has the ability to signal an alarm BEFORE the patient actually leaves the bed or chair. As the patient tries to get out of bed, the patient's weight rests on the long side bolsters, causing the change in pressure and therefore setting off the alarm. This occurs before the patient is actually off the mattress and out of bed.

This system will also sound the alarm if the bolster pressure increases when a patient is caught between the side rails of the frame and the bed mattress. This entrapment is of great concern to care givers as such entrapment can lead to serious injuries, sometimes even causing death.

In its most basic configuration, a simple "overlay" 30 including a flat sheet with attached side bolsters 12 could be placed directly on any hospital mattress, with a small electronic controller containing the compressor pump, sensors and a microprocessor attached to the bed frame F and connected to the inflatable side bolsters 12 via tubing.

Figure 3:
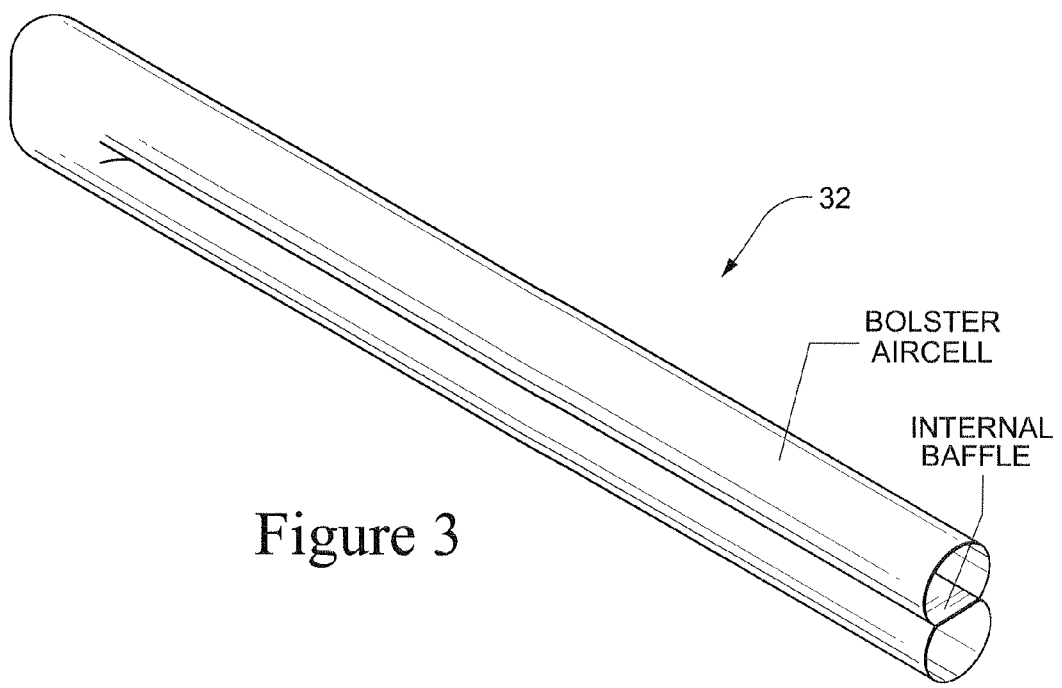
FIG. 3 is a perspective view of a baffled bolster.

The bolster air cells 12 can be of a singular tube like construction, but these tend to have a large round cross section and take up too much room between the side rails. An alternative bolster may be a baffled bolster 32 shown in FIG. 3, which would have a cross section higher than wide, therefore providing enough height over the mattress, but not taking up too much room between the side rails.

The exact size and design of the bolsters, as well as the bolster set pressure, and the pressure change in the air cells for a set period of time can vary according to requirements.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A bed exit detecting system cooperable with a mattress, the bed exit detecting system comprising:
    a pair of bolster air cells respectively positionable adjacent opposite sides of the mattress respectively facing the opposite sides of the mattress;
    a pressure source in fluid communication with the bolster air cells;
    a pressure sensor connected to the bolster air cells; and
    a signal processor communicating with the pressure sensor and the pressure source, wherein the signal processor includes an alarm that is activated when a predetermined pressure increase in one of the bolster air cells is detected by the pressure sensor.

2. A bed exit detecting system according to claim 1, wherein the bolster air cells extend along a full length of the mattress.

3. A bed exit detecting system according to claim 1, wherein the signal processor is programmed to maintain a predetermined pressure in the bolster air cells via the pressure source.

4. A bed exit detecting system according to claim 1, wherein the predetermined pressure increase is either a fixed value or is calculated internally based on patient weight and desired sensitivity.

5. A bed exit detecting system according to claim 1, wherein the signal processor is programmed to activate the alarm when the predetermined pressure increase is detected for a predetermined period of time.

6. A bed exit detecting system according to claim 5, wherein the predetermined period of time is about five seconds.

7. A bed exit detecting system according to claim 1, wherein the pressure sensor comprises a pressure transducer in fluid communication with the bolster air cells.

8. A bed exit detecting system according to claim 1, further comprising a mattress overlay to which the pair of bolster air cells is attached, the mattress overlay being sized to fit on top of the mattress with the bolster air cells extending along the opposite sides of the mattress.

9. A bed exit detecting system according to claim 8, further comprising a component housing containing the signal processor, the pressure source, and the pressure sensor, wherein the pressure source is connected to the bolster air cells via tubing.

10. A bed exit detecting system cooperable with a mattress, the bed exit detecting system comprising:
    a pair of bolster air cells respectively positionable adjacent opposite sides of the mattress;
    a pressure source in fluid communication with the bolster air cells;
    a pressure sensor connected to the bolster air cells; and
    a signal processor communicating with the pressure sensor and the pressure source,
wherein the signal processor includes an alarm that is activated when a predetermined pressure change in one of the bolster air cells is detected by the pressure sensor,
    wherein the bolster air cells comprise baffled bolsters having a cross section that is taller than it is wide.

11. A bed exit detecting system cooperable with a mattress, the bed exit detecting system comprising:
    a housing;
    a pair of bolster air cells under pressure and respectively positionable adjacent opposite sides of the mattress without interfering with a support function of the mattress;
    a pressure sensor mounted in the housing and communicating with the bolster air cells; and
    a signal processor mounted in the housing and communicating with the pressure sensor,
wherein the signal processor includes an alarm that is activated when a predetermined pressure increase in one of the bolster air cells is detected by the pressure sensor.

12. A bed exit detecting system according to claim 11, further comprising a pressure source mounted in the housing and in fluid communication with the bolster air cells, wherein the signal processor is programmed to maintain a predetermined pressure in the bolster air cells via the pressure source.

13. A bed exit detecting system according to claim 11, wherein the signal processor is programmed to activate the alarm when the predetermined pressure increase is detected for a predetermined period of time.

14. A hospital bed comprising:
    a bed frame;
    a mattress secured to the bed frame; and
    a bed exit detecting system, the bed exit detecting system including:
        a housing secured to the bed frame,
        a pair of bolster air cells attached to a mattress overlay, the mattress overlay being fit on top of the mattress, wherein the bolster air cells are under pressure and respectively positioned adjacent opposite sides of the mattress respectively facing the opposite sides of the mattress,
        a pressure sensor mounted in the housing and communicating with the bolster air cells, and
        a signal processor mounted in the housing and communicating with the pressure sensor, wherein the signal processor includes an alarm that is activated when a predetermined pressure increase in one of the bolster air cells is detected by the pressure sensor.

15. A hospital bed according to claim 14, further comprising a pressure source mounted in the housing and in fluid communication with the bolster air cells, wherein the signal processor is programmed to maintain a predetermined pressure in the bolster air cells via the pressure source.

16. A hospital bed according to claim 14, wherein the signal processor is programmed to activate the alarm when the predetermined pressure increase is detected for a predetermined period of time.

* * * * *

UNITED STATES PATENT AND TRADEMARK OFFICE
CERTIFICATE OF CORRECTION

| | | |
|---|---|---|
| PATENT NO. | : 8,042,206 B2 | |
| APPLICATION NO. | : 12/558142 | |
| DATED | : October 25, 2011 | |
| INVENTOR(S) | : Genaro | |

It is certified that error appears in the above-identified patent and that said Letters Patent is hereby corrected as shown below:

Column 2, line 17, delete "a" and insert --at--.

Signed and Sealed this
Third Day of January, 2012

David J. Kappos
*Director of the United States Patent and Trademark Office*